(12) United States Patent
Capote et al.

(10) Patent No.: US 10,729,556 B2
(45) Date of Patent: Aug. 4, 2020

(54) SPINAL IMPLANT SYSTEM AND METHOD

(71) Applicant: Warsaw Orthopedic, Inc., Warsaw, IN (US)

(72) Inventors: Cristian A. Capote, Memphis, TN (US); Jonathan E. Blackwell, Lakeland, TN (US); Anthony J. Melkent, Memphis, TN (US); Neel Anand, Los Angeles, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/958,253

(22) Filed: Apr. 20, 2018

(65) Prior Publication Data

US 2018/0235768 A1 Aug. 23, 2018

Related U.S. Application Data

(63) Continuation of application No. 15/151,717, filed on May 11, 2016, now Pat. No. 10,034,771.

(51) Int. Cl.
| | |
|---|---|
| *A61F 2/30* | (2006.01) |
| *A61F 2/44* | (2006.01) |
| *A61F 2/46* | (2006.01) |
| *A61B 17/80* | (2006.01) |
| *A61B 17/70* | (2006.01) |

(52) U.S. Cl.
CPC ............ *A61F 2/447* (2013.01); *A61B 17/808* (2013.01); *A61B 17/8042* (2013.01); *A61F 2/30749* (2013.01); *A61F 2/4455* (2013.01); *A61F 2/4611* (2013.01); *A61B 17/7059* (2013.01); *A61F 2002/30265* (2013.01); *A61F 2002/30401* (2013.01); *A61F 2002/30507* (2013.01); *A61F 2002/30553* (2013.01); *A61F 2002/30578* (2013.01); *A61F 2002/30593* (2013.01); *A61F 2002/30836* (2013.01)

(58) Field of Classification Search
CPC .... A61F 2/447; A61F 2/4611; A61F 2/30749; A61F 2/4455; A61F 2002/30265; A61F 2002/4475; A61F 2002/30401; A61F 2002/30507; A61F 2002/30553; A61F 2002/30578; A61F 2002/30536; A61B 17/7059; A61B 17/808; A61B 17/8042
USPC ...................... 623/17.11–17.16; 606/246–279
See application file for complete search history.

(56) References Cited

U.S. PATENT DOCUMENTS

| | | | |
|---|---|---|---|
| 5,755,796 | A | 5/1998 | Ibo et al. |
| 6,106,557 | A | 8/2000 | Robioneck et al. |
| 6,156,037 | A | 12/2000 | Lehuec et al. |
| 6,235,059 | B1 | 5/2001 | Benezech et al. |
| 6,508,818 | B2 | 1/2003 | Steiner et al. |

(Continued)

*Primary Examiner* — Pedro Philogene
(74) *Attorney, Agent, or Firm* — Sorell, Lenna & Schmidt, LLP (57) ABSTRACT

A spinal implant includes an implant body extending between an anterior surface and a posterior surface. The implant body includes a first vertebral engaging surface and a second vertebral engaging surface. The implant body defines a cavity. A plate is connectable with the implant body via a coupling member adjacent the cavity and is translatable relative thereto. The coupling member has a portion including a frangible torque limit. The plate defines at least one opening oriented to implant a fastener with tissue. Systems, spinal constructs, surgical instruments and methods are disclosed.

21 Claims, 8 Drawing Sheets

(56) References Cited

U.S. PATENT DOCUMENTS

| | | | |
|---|---|---|---|
| 7,172,627 B2* | 2/2007 | Fiere | A61B 17/7059 |
| | | | 623/17.11 |
| 7,621,938 B2 | 11/2009 | Molz, IV | |
| 7,758,616 B2* | 7/2010 | LeHuec | A61B 17/1671 |
| | | | 606/246 |
| 8,480,747 B2 | 7/2013 | Melkent et al. | |
| 10,034,771 B2* | 7/2018 | Capote | A61F 2/447 |
| 2002/0095155 A1 | 7/2002 | Michelson | |
| 2003/0195632 A1 | 10/2003 | Foley et al. | |
| 2005/0101960 A1* | 5/2005 | Fiere | A61B 17/7059 |
| | | | 623/17.11 |
| 2008/0051890 A1 | 2/2008 | Waugh et al. | |
| 2008/0161925 A1 | 7/2008 | Brittan et al. | |
| 2008/0183294 A1 | 7/2008 | Adl | |
| 2008/0312742 A1 | 12/2008 | Abernathie | |
| 2009/0306779 A1 | 12/2009 | Ahn | |
| 2013/0218276 A1 | 8/2013 | Fiechter et al. | |
| 2013/0345813 A1* | 12/2013 | Frank | A61F 2/447 |
| | | | 623/17.16 |
| 2017/0245900 A1* | 8/2017 | Rezach | A61B 17/7055 |

\* cited by examiner

SPINAL IMPLANT SYSTEM AND METHOD

CROSS-REFERENCE TO RELATED APPLICATIONS

This application is a continuation of application U.S. patent application Ser. No. 15/151,717, filed on May 11, 2016, which is hereby incorporated by reference herein, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as degenerative disc disease, disc herniation, spondylolisthesis, stenosis, osteoporosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Certain spinal surgery approaches utilize a direct lateral approach to access intervertebral spaces, however, these techniques present certain challenges due to the location of musculature and neural structures embedded therein. This disclosure describes an improvement over these prior technologies.

SUMMARY

In one embodiment, a spinal implant is provided. The spinal implant includes an implant body extending between an anterior surface and a posterior surface. The implant body includes a first vertebral engaging surface and a second vertebral engaging surface. The implant body defines a cavity. A plate is connectable with the implant body via a coupling member adjacent the cavity and is translatable relative thereto. The coupling member has a portion including a frangible torque limit. The plate defines at least one opening oriented to implant a fastener with tissue. In some embodiments, systems, spinal constructs, surgical instruments and methods are provided.

In one embodiment, a spinal implant includes an implant body extending between an anterior surface and a posterior surface. The implant body includes a first vertebral engaging surface and a second vertebral engaging surface. A plate is connectable with the implant body via a coupling member and defines a single opening oriented to implant a fastener with tissue.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure are employed with a spinal joint and fusion, for example, with a cervical, thoracic, lumbar and/or sacral region of a spine.

In some embodiments, the present surgical system includes an interbody implant. In some embodiments, the interbody implant includes an interbody cage. In some embodiments, the surgical system includes a plate that is affixed to an interbody implant and a superior vertebral body and/or an inferior vertebral body adjacent an interbody space of vertebrae. In some embodiments, the surgical system includes an interbody implant connected with a plate, locks and/or insertion mechanisms. In some embodiments, the surgical system includes one or more radiographic markers selectively disposed with one or more components of the surgical system. In some embodiments, the surgical system includes a hyper-lordotic interbody implant configured to achieve lordosis of vertebrae in a range of greater than 12 angular degrees.

In some embodiments, the surgical system includes instrumentation that is employed with a method to anchor an interbody implant within an interbody space of vertebrae. In some embodiments, the method includes the step of disposing a hyper-lordotic interbody implant configured to achieve lordosis of vertebrae in a range of greater than 12 angular degrees within an interbody space. In some embodiments, the present system avoids migration of the interbody implant within the interbody space. In some embodiments, the interbody implant includes a plate that is modularly or removably connected to the interbody implant via a set screw. In some embodiments, the plate is attached to a lateral or antero-lateral aspect of a vertebra outside the interbody space using a bone screw. In some embodiments, the surgical system includes a plate that is not attached with the interbody implant.

In some embodiments, the surgical system includes a plate that is connected to an interbody implant and the plate includes a single bone screw engageable with a vertebral body adjacent an interbody space of vertebrae. In some embodiments, the single bone screw is configured to anchor the interbody implant and/or plate with tissue. In some embodiments, the single bone screw includes a buttress configuration. In some embodiments, the interbody implant is not attached with the plate.

In some embodiments, the surgical system includes a plate that is connected to an interbody implant and the plate includes a two bone screw assembly engageable with vertebrae adjacent an interbody space of the vertebrae. In some embodiments, the two bone screw assembly is configured to anchor the interbody implant and/or plate with tissue. In some embodiments, the two bone screw assembly is configured to provide stabilization between vertebra. In some embodiments, the surgical system includes a plate that is connected to an interbody implant and the plate includes a four bone screw assembly engageable with vertebrae adjacent an interbody space of the vertebrae. In some embodiments, the four bone screw assembly is configured to anchor the interbody implant and/or plate with tissue. In some embodiments, the four bone screw assembly is configured to provide stabilization between vertebra.

In some embodiments, the surgical system includes a plate that is connected to an interbody implant via a set screw. In some embodiments, the set screw includes a break off portion or head that is removable, separable or frangible at a selected torque limit. In some embodiments, the surgical system is employed with a method such that the interbody implant and plate assembly is positioned with an interbody space and bone screws attach the plate to tissue. In some embodiments, the method includes the step of breaking off the set screw head to release the assembly from a surgical inserter. In some embodiments, the surgical inserter includes a screw driver.

In some embodiments, the surgical system is configured to resist and/or prevent migration of the interbody implant within an interbody space. In some embodiments, the surgical system includes a plate that is modularly or removably connected to the interbody implant by a set screw. In some embodiments, the plate is attached to a lateral or antero-lateral portion of vertebra outside the interbody space using a bone screw. In some embodiments, the interbody implant is a standalone interbody implant.

In some embodiments, the surgical system includes a plate that is connected to an interbody implant via a set screw, the plate including one or more bone screws for fixation with tissue. In some embodiments, the plate includes an element to resist and/or prevent backout of the screws from the interbody implant and plate assembly and/or tissue. In some embodiments, the element includes a surface that is disposed with the set screw and a bone screw to resist and/or prevent backout of the set screw and the bone screw. In some embodiments, the surface includes a cam lock capture member that is disposed with the set screw and a bone screw to resist and/or prevent backout of the set screw and the bone screw. In some embodiments, the surface is movable into alignment with the set screw and a bone screw to resist and/or prevent backout of the set screw and the bone screw. In some embodiments, the surface is rotatable into alignment with the set screw and a bone screw.

In some embodiments, the surgical system includes an interbody implant and plate assembly having two bone screws. In some embodiments, the interbody implant and plate assembly includes an element to resist and/or prevent backout of the two bone screws and the set screw from the interbody implant and plate assembly and/or tissue. In some embodiments, the surgical system includes an interbody implant and plate assembly having four bone screws. In some embodiments, the interbody implant and plate assembly includes an element to resist and/or prevent backout of the four bone screws and the set screw from the interbody implant and plate assembly and/or tissue.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 1:
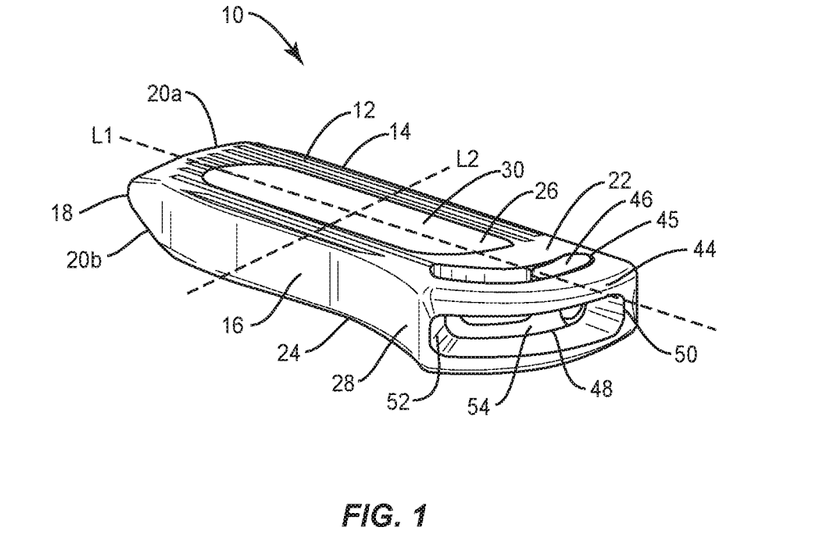
FIG. 1 is a perspective view of components of one embodiment of a surgical system in accordance with the principles of the present disclosure.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO₄ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 3:
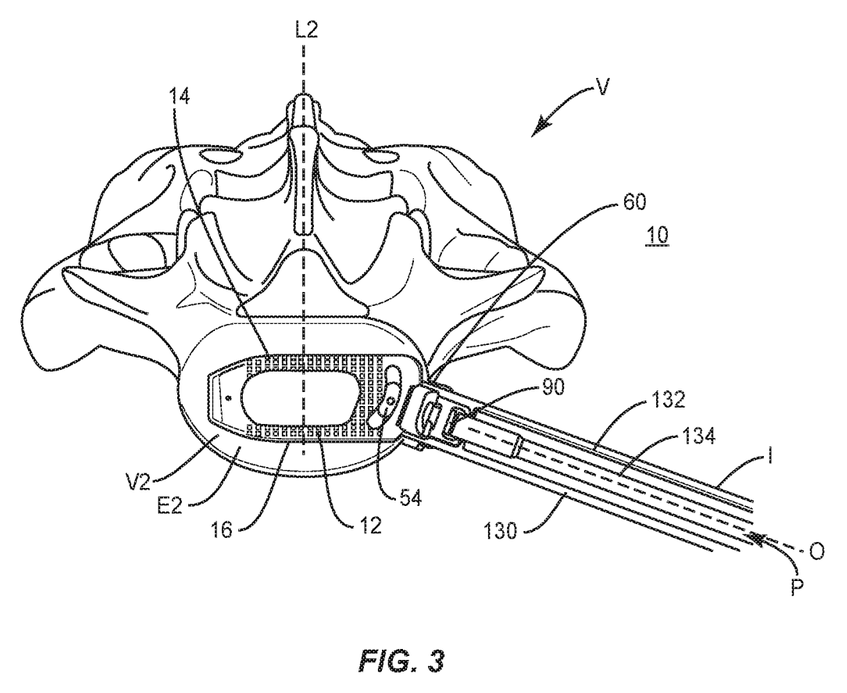
FIG. 3 is a plan view of components of one embodiment of a surgical system in accordance with the principles of the present disclosure disposed with vertebrae.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site of a patient, which includes, for example, a spine having vertebrae V, as shown in FIG. 3. In some embodiments, a surgical pathway P to a surgical site is formed via an oblique lateral interbody fusion (OLIF) or a direct lateral interbody fusion (DLIF) procedure. In some embodiments, the implant can include spinal constructs, such as, for example, bone fasteners, spinal rods, connectors and/or plates.

Figure 4:
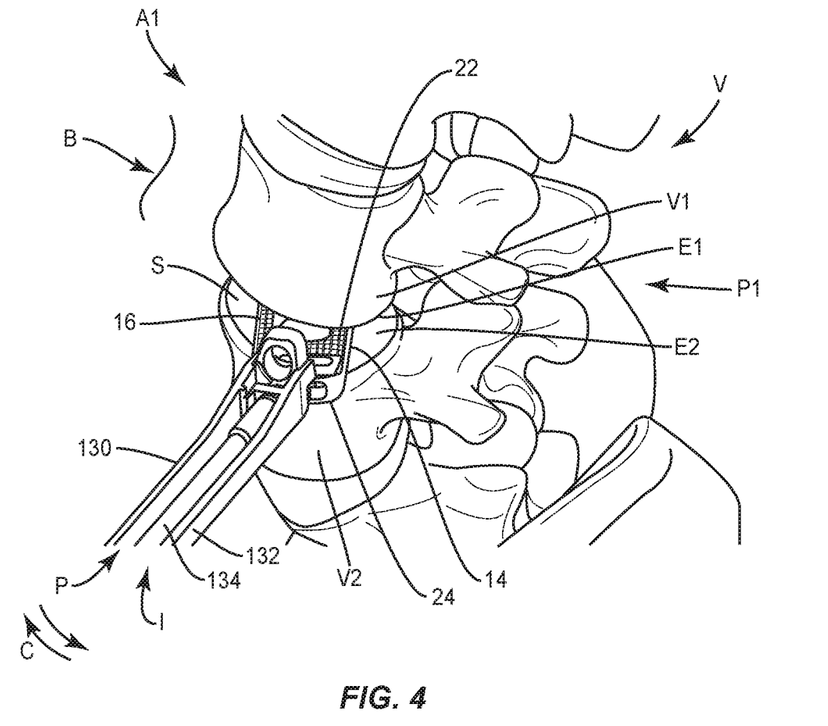
FIG. 4 is a perspective view of the components and vertebrae shown in FIG. 3.

Spinal implant system 10 includes an implant body, such as, for example, an interbody cage 12. Cage 12 extends between a posterior surface 14 and an anterior surface 16 and defines an axis L1. Posterior surface 14 is configured to face a posterior side of a subject body B and be disposed adjacent a posterior portion of vertebrae, such as, for example, a posterior portion P1 of one or more intervertebral spaces of vertebrae V, as shown in FIG. 4. Anterior surface 16 is configured to face an anterior side of subject body B and be disposed adjacent an anterior portion of vertebrae, such as, for example an anterior portion A1 of one or more intervertebral spaces of vertebrae V.

In some embodiments, cage 12 includes a convex distal end, such as, for example, a bullet nose 18 to facilitate insertion by a surgeon. In some embodiments, cage 12 may include chamfers, such as, for example, cut outs 20a, 20b disposed on bullet nose 18 such that cage 12 may be placed in an intervertebral space to avoid impinging on various structures in or adjacent vertebral tissue, such as, for example, a spinal foramina.

In some embodiments, cage 12 includes any number and configuration of radiopaque markers (such as tantalum pins (not shown)) for visualizing a position of cage 12 using fluoroscopy during insertion, manipulation and implantation thereof. In some embodiments, the markers may be placed obliquely on bullet nose 18, in sidewalls of cage 12 adjacent surfaces 14, 16 and/or in a proximal end of cage 12. In some embodiments, the markers may be placed parallel, oblique to and/or perpendicular to surfaces 14, 16 as required to properly visualize the position of cage 12 relative to surgical pathway P and/or relative to an oblique axis O, as shown in FIG. 3, to facilitate placement of cage 12, as described herein.

Cage 12 includes a vertebral engaging surface 22 and a vertebral engaging surface 24. Surface 22 may be substantially planar and configured to engage endplate tissue of a vertebral body, such as, for example, an endplate E1 of a vertebral level V1, as shown in FIG. 4. Surface 24 may be substantially planar and configured to engage endplate tissue of a vertebral body, such as, for example, an endplate E2 of a vertebral level V2. In some embodiments, surface 22 and/or surface 24 may be rough, textured, porous, semi-porous, dimpled, knurled, toothed, grooved and/or polished to facilitate engagement with tissue.

In some embodiments, surface 22 and/or surface 24 may be partially convex along axis L1 and/or at least partially convex in a direction substantially perpendicular to an axis L2 (i.e., from surface 16 to surface 14). In some embodiments, surface 22 and/or surface 24 may be angled along axis L1 or angled perpendicular to axis L1 such that anterior surface 16 is taller than posterior surface 14 such that cage 12 may be capable of creating and/or augmenting lateral or lordotic curvature in a spine when implanted. In some embodiments, surface 22 and surface 24 are disposed at a relative angular orientation to include a hyper-lordotic configuration to correct lumbar lordosis in situations where a natural curve of a lumbar region of the back is accentuated. In some embodiments, surface 22 and surface 24 are disposed at a relative angular orientation in a range of greater than 12 degrees.

In some embodiments, vertebral tissue includes intervertebral tissue, endplate surfaces and/or cortical bone. In some embodiments, surface 22 and/or surface 24 may be coated with materials suitable for facilitating or encouraging bony ongrowth or fusion including but not limited to titanium and HA coatings. In some embodiments, a titanium coating is applied to surface 22 and/or surface 24 in a porous layer using plasma spray technology.

Cage 12 has a substantially rectangular configuration and includes an inner surface 26 and an outer surface 28. Surface 26 defines an opening 30 configured to receive an agent, which may include bone graft (not shown) and/or other materials, as described herein, for employment in a fixation or fusion treatment. In some embodiments, a plan geometry of cage 12 may have various configurations, such as, for example, oval, round, cylindrical, oblong, triangular, rectangular, polygonal having planar or arcuate side portions, irregular, uniform, non-uniform, consistent, variable, horseshoe shape, U-shape or kidney bean shape.

Outer surface 28 includes an oblique surface 44 that defines a cavity, such as, for example, an elongated opening 45. Elongated opening 45 defines a track 46. Oblique surface 44 is oriented with cage 12 and in substantial alignment with surgical pathway P, as shown in FIGS. 3 and 4. Track 46 is in open communication with surface 44 to define a track pathway 48 that facilitates translation and/or rotation of a plate connected with cage 12, as described herein. In some embodiments, pathway 48 is arcuate in shape. In some embodiments, track 46 includes a varying radius of curvature. Track 46 includes a limit, such as, for example, a lateral axis limit 50 and a limit, such as, for example, an oblique axis limit 52. Limits 50, 52 provide a range of translation relative to cage 12 along track 46 and/or pathway 48, as discussed herein.

Member 54 is slidably engageable with track 46 for translation relative to cage 12 along track pathway 48. In some embodiments, member 54 is movable along track pathway 48 for translation substantially along axis L2 and/or transverse to axis L1. In some embodiments, member 54 is movable along track pathway 48 for rotation about axis L2 and/or axis L1. In some embodiments, track pathway 48 includes an arcuate configuration. In some embodiments, track pathway 48 extends along an arcuate configuration that is substantially concentric with track 46 and/or a lateral surface of cage 12. In some embodiments, track 46, surface 44 and/or track pathway 48 may be arcuate with a single radius defining an arcuate configuration. In some embodiments, track 46, surface 44 and/or track pathway 48 may be arcuate with multiple radii defining one or more portions of an arcuate configuration.

In some embodiments, track 46, surface 44 and/or track pathway 48 may extend along a pathway having various configurations corresponding to an overall shape of cage 12, such as, for example, round, cylindrical, oblong, triangular, rectangular, polygonal having planar or arcuate side portions, irregular, uniform, non-uniform, consistent, variable, horseshoe shape, U-shape or kidney bean shape. In some embodiments, the surfaces of cage 12 may be rough, textured, porous, semi-porous, dimpled, knurled, toothed, grooved and/or polished for selective translation of member 54.

Figure 2:
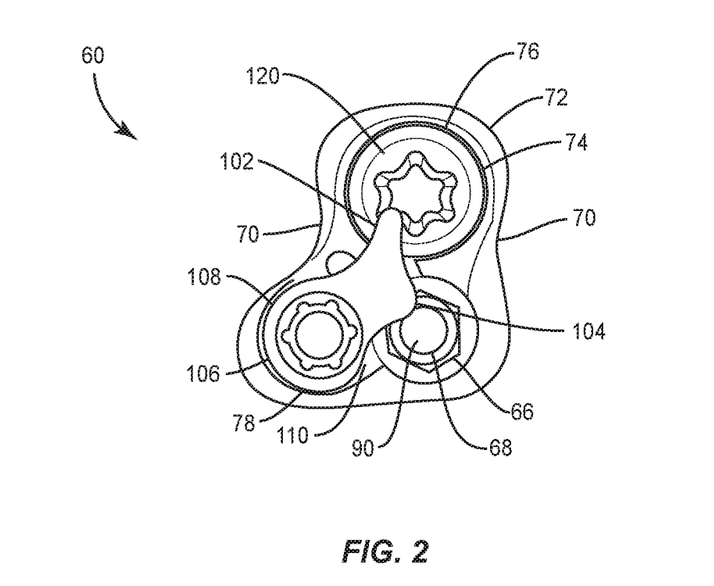
FIG. 2 is a side view of components of one embodiment of a surgical system in accordance with the principles of the present disclosure.
Figure 8:
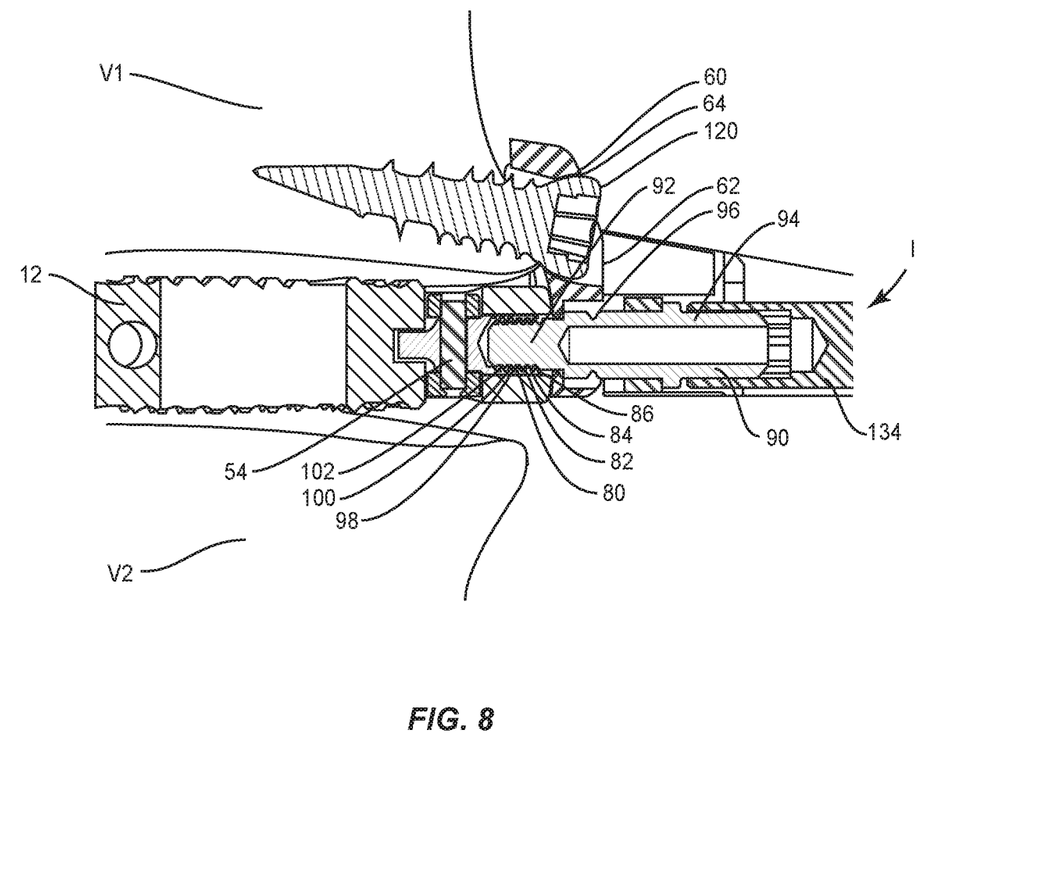
FIG. 8 is a cross section view of the components and vertebrae shown in FIG. 5.

Spinal implant system 10 includes a plate 60, as shown in FIG. 2. Plate 60 includes a surface 62 and a surface 64, as shown in FIG. 8. In some embodiments, plate 60 includes a substantially rectangular configuration. In some embodiments, plate 60 can be variously configured, such as, for example, tubular, oval, oblong, triangular, square, polygonal, irregular, uniform, non-uniform, variable, hollow and/or tapered. In some embodiments, plate 60 may be attached with cage 12 prior to implantation, in vivo or in situ. In some embodiments, plate 60 is removably connected with cage 12.

Plate 60 includes a surface 66 that defines an opening 68. Opening 68 extends between surfaces 62, 64. Opening 68 is configured to receive a coupling member, such as, for example, a set screw 90, as described herein. Opening 68 is configured for alignment with track pathway 48 and track 46 and facilitates engagement of set screw 90 with member 54, as described herein. Plate 60 includes instrument engagement surfaces 70. Surfaces 70 are configured to engage a surgical instrument, such as, for example, an inserter I to facilitate insertion and disposal of the components of spinal implant system 10 at a surgical site, as described herein.

Figure 5:
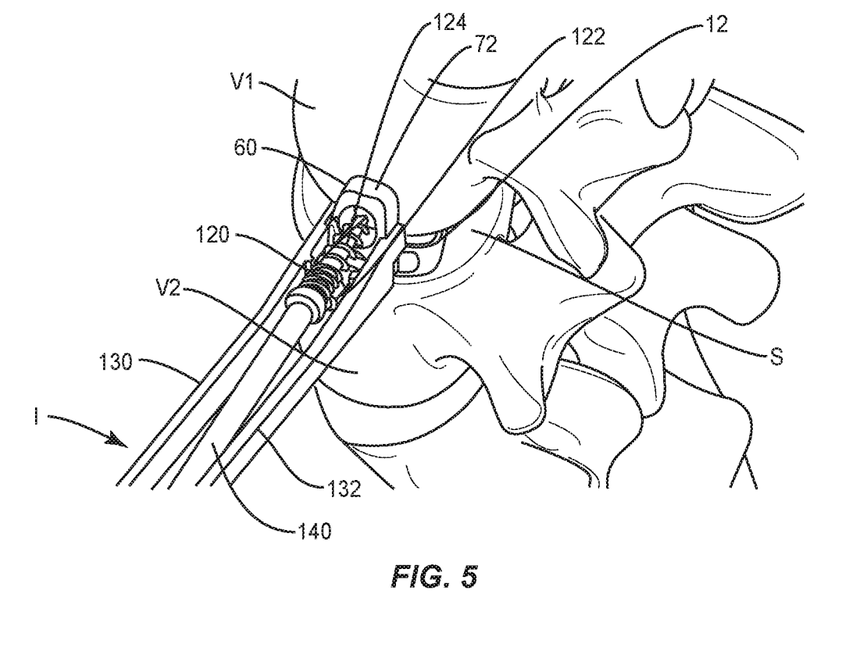
FIG. 5 is a perspective view of components of one embodiment of a surgical system in accordance with the principles of the present disclosure disposed with vertebrae.

Plate 60 includes a portion 72 configured to engage a vertebral level. Plate 60 includes a surface 74 that defines an opening 76. Opening 76 extends between surfaces 62, 64. Opening 76 is configured to receive a fastener 120, as described herein. Opening 76 orients fastener 120 for fixation with tissue, such as, for example, a vertebral level V1, as shown in FIG. 5. In some embodiments, a surgical instrument or tool, as described herein, manipulates and/or rotates plate 60 about cage 12, opening 68 and/or tissue such that opening 76 is aligned with selected vertebral tissue, for example, a superior vertebral body such as vertebral level V1 or an inferior vertebral body such as vertebral level V2 for orienting a fastener for fixation of cage 12 and/or plate 60 with the selected vertebral level. In some embodiments, a surgical instrument or tool is engageable with portion 72, surface 74 and/or surface 66 to rotate plate 60.

In some embodiments, plate 60 includes an element, such as, for example, a capture tab 78. In some embodiments, tab 78 is configured as a rotating cam lock having a protrusion 102 and a protrusion 104. Protrusion 102 is configured to extend over and/or overlap all or a portion of fastener 120 to resist and/or prevent backout of fastener 120 from plate 60 and/or tissue through opening 76, for example, which can be caused by growth, movement and adjustments of vertebrae. Protrusion 104 is configured to extend over and/or overlap all or a portion of set screw 90 to resist and/or prevent backout of set screw 90 from plate 60 and/or cage 12 through opening 68.

Figure 9:
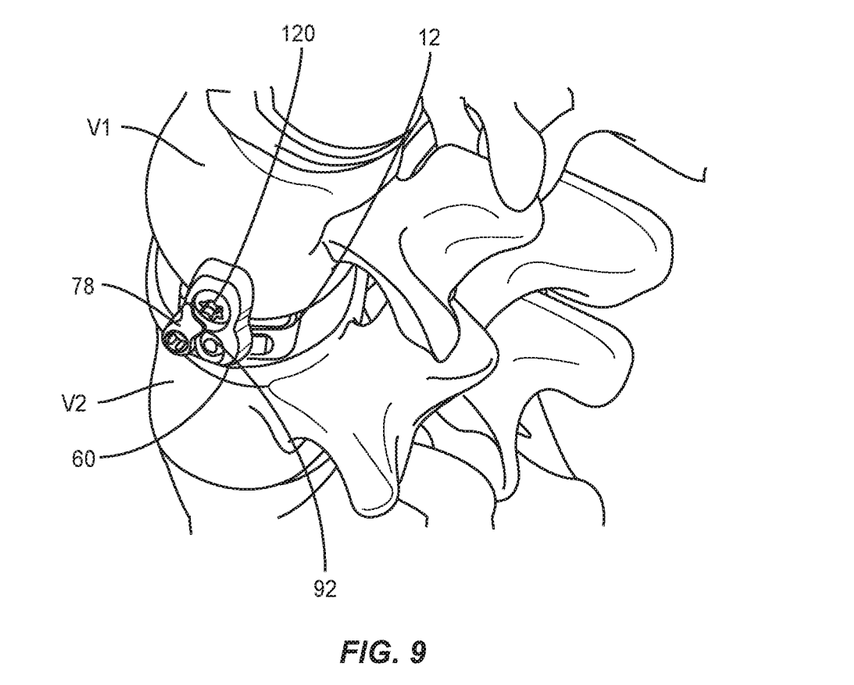
FIG. 9 is a perspective view of the components and vertebrae shown in FIG. 5.
Figure 10:
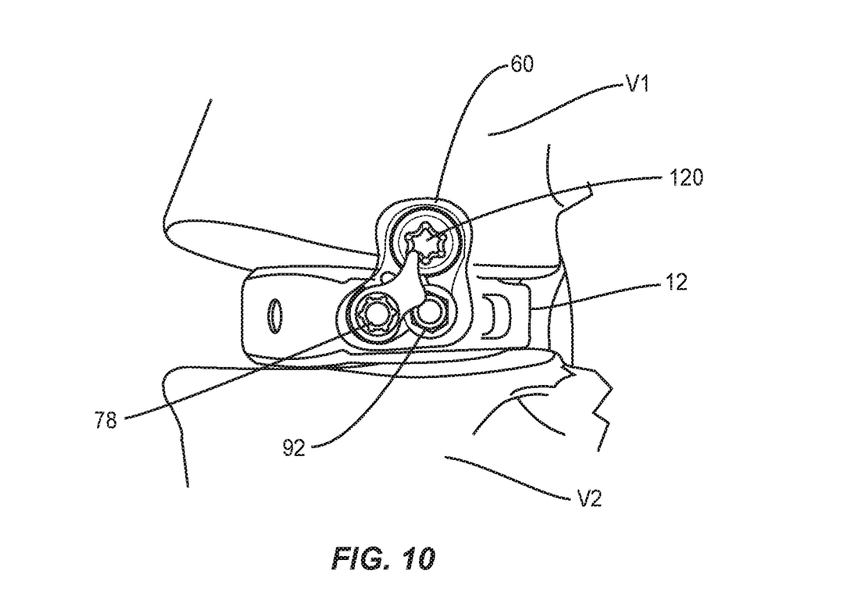
FIG. 10 is a side view of the components and vertebrae shown in FIG. 5.

Tab 78 includes a portion 106 configured to facilitate movement of protrusions 102, 104 between a non-locking orientation, as shown in FIG. 9, and a locking orientation, as shown in FIG. 10, relative to fastener 120 and set screw 90. In some embodiments, portion 106 includes a surface that defines a cavity 108 having a hexagonal geometry configured for engagement with a similarly shaped surgical tool, such as, for example, a portion of inserter I, as described herein. In some embodiments, cavity 108 includes a cruciform, phillips, square, hexalobe, polygonal or star cross sectional configuration for disposal of a correspondingly shaped portion of a surgical tool. In some embodiments, tab 78 is disposed within a cavity 110 of plate 60 for rotation relative thereto. In some embodiments, tab 78 is configured for rotation such that protrusions 102, 104 move into alignment with fastener 120 and/or set screw 90 to resist and/or prevent fastener 120 and set screw 90 from disengaging from cage 12 and/or a vertebra.

In some embodiments, member 54 includes a spheroidal joint, such as, for example, a ball screw 80 having an elongated post 82, as shown in FIG. 8. Screw 80 is configured to provide freedom of movement and/or toggle of plate 60 relative to cage 12. Screw 80 is configured for engagement with and translation along track 46 and/or track pathway 48. Post 82 includes a surface 84 that defines a cavity 86. Surface 84 is configured for engagement with set screw 90 to fix plate 60 with cage 12. In some embodiments, set screw 90 is configured to draw plate 60 and cage 12 together into an assembled orientation during insertion. In some embodiments, screw 80 provides translation of plate 60 relative to cage 12 in a plurality of orientations in multiple planes.

In some embodiments, surface 44 and/or member 54 can comprise a dovetail or t-slot sliding attachment mechanism can be utilized for connection plate 60 with cage 12. In some embodiments, plate 60 is freely translatable within the patient body such that plate 60 is configured for dynamic translation. In some embodiments, plate 60 is positioned within the patient body and locked into a fixed position with tissue and/or cage 12. In some embodiments, plate 60 is configured for selective positioning with a subject body for adapting to the configuration of the tissue surfaces of vertebrae, as well as provide range of motion limits 50, 52 for plate 60.

Screw 90 includes a portion 92 and a portion 94, as shown in FIG. 8. Portions 92, 94 are connected at a reduced diameter portion 96 that is frangibly connected to portion 94. In some embodiments, portion 92 is configured for a threaded engagement with surface 84. In some embodiments, portions 92, 94 are fabricated from a fracturing and/or frangible material such that manipulation of portion 94 relative to portion 92 can fracture and separate portion 94 from portion 92 at a predetermined force and/or torque limit, as described herein. In some embodiments, as force and/or torque is applied to portion 94 by inserter I and resistance increases, for example, due to fixation of portion 92 with surface 84 of cavity 86, as described herein, the predetermined torque and force limit is approached. In some embodiments, portions 92, 94 include offset hex geometries.

In some embodiments, portions 92, 94 can fracture and separate at a predetermined force or torque limit, which may be in a range of approximately 20 Newton centimeters (N-cm) to 50 N-cm. In some embodiments, portions 92, 94 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 92, 94.

Portion 92 includes a shaft 98 having an outer surface 100. Surface 100 includes a thread form 102 configured for engagement with surface 84. In some embodiments, thread form 102 is continuous along surface 100. In some embodiments, thread form 102 may include a single thread turn or a plurality of discrete threads. In some embodiments, other penetrating elements may be located on shaft 98, such as, for example, a nail configuration, barbs, expanding elements, raised elements, ribs, and/or spikes to facilitate engagement of shaft 98.

In some embodiments, portion 94 includes an end having a hexagonal geometry configured for engagement with a similarly shaped surgical tool, such as, for example, a portion of inserter I, as described herein. In some embodiments, end 94 includes a cruciform, phillips, square, hexalobe, polygonal or star cross sectional configuration for disposal of a correspondingly shaped portion of a tool. Set screw 90 is configured to removably couple plate 60 with cage 12, as described herein.

Spinal implant system 10 includes one or more fasteners 120 for attaching plate 60 and/or cage 12 to tissue, as described herein. In some embodiments, fastener 120 may be engaged with tissue, such as, for example, the bony structures of a vertebral body in various orientations, such as, for example, series, parallel, offset, staggered and/or alternate vertebral levels. In some embodiments, one or more of fasteners 120 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Fastener 120 comprises a portion, such as, for example, a head 122 and a portion, such as, for example, an elongated shaft 124 configured for penetrating tissue. Head 122 includes an engagement portion configured for engagement with a surgical instrument, as described herein. Shaft 124 has a cylindrical cross section configuration and includes an outer surface having an external thread form. In some embodiments, the external thread form may include a single thread turn or a plurality of discrete threads. In some embodiments, other engaging structures may be located on shaft 124, such as, for example, a nail configuration, barbs, expanding elements, raised elements and/or spikes to facilitate engagement of shaft 124 with tissue.

In some embodiments, all or only a portion of shaft 124 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 124 may include one or a plurality of openings. In some embodiments, all or only a portion of the outer surface of shaft 124 may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of shaft 124 may be cannulated.

In some embodiments, spinal implant system 10 may comprise various surgical instruments, such as, for example, drivers, extenders, reducers, spreaders, distracters, blades, forceps, elevators and drills, which may be alternately sized and dimensioned, and arranged as a kit. In some embodiments, spinal implant system 10 may comprise the use of microsurgical and image guided technologies, such as, for example, surgical navigation components employing emitters and sensors, which may be employed to track introduction and/or delivery of the components of spinal implant system 10 and the surgical instruments described to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, as shown in FIGS. 3-10, spinal implant system 10, similar to the systems and methods described herein, is employed with a surgical procedure for treatment of a spinal disorder, such as those described herein, affecting a section of a spine of a patient. The components of spinal implant system 10 are employed with a surgical procedure for treatment of a spinal disorder affecting a section of a spine of a patient, for example, to treat the affected section of vertebrae V of a patient utilizing an OLIF or DLIF procedure.

A retractor (not shown) is disposed in communication with surgical pathway P for spacing tissue. In some embodiments, spinal implant system 10 may include retractors such that no further probe is required. In some embodiments, spinal implant system 10 may include retractors constrained via a frame or semi-constrained using an elastic or partial frame. In some embodiments, retractor blades are inserted simultaneously as part of a unitary retractor instrument around one or more intervertebral spaces to protect vessels.

In some embodiments, an annulotomy and/or discectomy is performed with a surgical instrument with x-ray confirmation of the starting point that is central on one or more intervertebral spaces. In some embodiments, spinal implant system 10 includes a semi-constrained retractor that facilitates minimal tissue pressures on surrounding abdominal structures and provides flexibility such that its blades rotate on a fixed pin allowing greater degrees of freedom of movement and working angles for a practitioner.

A probe is passed into the disc space to secure its location. In some embodiments, the oblique angle and lordotic angle of the probe as it enters the disc space is assessed pre-operatively and measured intra-operative using image guidance or using a mechanical or digital protractor. Fluoroscopy, image guidance and/or surgical navigation, as described herein, is used to confirm proper probe alignment into the disc space. In some embodiments, a guide wire is placed through a cannula into the disc space and positioning is confirmed with fluoroscopy. Instruments, such as, for example, a Cobb, mallet, shaver, serrated curettes, rasp, a ring curette, a uterine curette and/or combo tools are utilized to perform a discectomy of the disc space. The instruments enter the patient body obliquely through the retractor and can be turned orthogonally to allow the surgeon to work orthogonally across the disc space. The disc space is distracted until adequate disc space height is obtained.

In some embodiments, a discectomy is performed via surgical pathway P. In some embodiments, trial implants are delivered along surgical pathway P and used to distract one or more intervertebral spaces and apply appropriate tension in the intervertebral space allowing for indirect decompression. In some embodiments, a direct decompression of the disc space is performed by removing a portion of a herniated disc. In some embodiments, the size of cage 12 is selected after trialing and cage 12 is visualized by fluoroscopy and oriented before malleting into the intervertebral space. Trialing is utilized to establish a starting point for cage 12 insertion. In some embodiments, an anterior longitudinal ligament (ALL) release procedure can be performed using an OLIF or a DLIF approach post-discectomy. For example, loosening the ALL can be performed by placing holes or partial cuts in the ALL such that the OLIF surgical pathway is immediately closer to the ALL.

A pilot hole(s) or the like is made in selected vertebra V1 of vertebrae V adjacent the intervertebral space, via surgical pathway P, for receiving bone fastener 120. Inserter I is attached with cage 12 and/or plate 60, as described herein. Inserter I delivers cage 12 and plate 60 along surgical pathway P adjacent to a surgical site for implantation adjacent the intervertebral space between vertebrae V1 and V2, as shown in FIGS. 3 and 4. In some embodiments, inserter I includes a navigation component to facilitate placement of cage 12 and plate 60 between vertebrae V1, V2.

During insertion, inserter I is attached with plate 60 by arms 130, 132. Arms 130, 132 are configured to engage surfaces 70 to facilitate manipulation of plate 60 relative to cage 12. Inserter I is connected with set screw 90 by a driver 134. Portion 94 of set screw 90 is engaged with driver 134. Driver 134 and set screw 90 are utilized to provisionally fix plate 60 and cage 12 with inserter I. Tightening of set screw 90 causes cage 12, plate 60 and inserter I to be drawn together and held in an assembled orientation during insertion.

Cage 12 and plate 60 are inserted through the retractor adjacent the surgical site. Anterior surface 16 faces an anterior side of the patient body adjacent anterior portion A1 and posterior surface 14 faces a posterior side of the patient body adjacent posterior portion P1, as described herein. Surface 22 engages endplate tissue of endplate E1 and surface 24 engages endplate tissue of endplate E2. In some embodiments, after implantation of cage 12 and plate 60, a practitioner can loosen the connection of inserter I, cage 12 and plate 60. This configuration allows plate 60 to rotate and translate relative to cage 12, which provides cage 12 and plate 60 relative freedom of movement such that the practitioner can maneuver the spinal construct for final placement of cage 12 and/or plate 60.

Inserter I is an adaptable instrument configured to perform multiple applications during a surgical procedure. In some embodiments, inserter I can prepare and/or create a cavity in tissue, such as, for example, bone. In some embodiments, inserter I guides a surgical instrument, such as, for example, a drill, tap and/or an awl, as well as guiding fasteners to penetrate tissue. In some embodiments, inserter I is a guide that holds plate 60 and cage 12 together. Surgical instruments including an awl, a tap and screws can be passed through inserter I.

In some embodiments, inserter I is utilized to apply a force to plate 60 such that plate 60 is translatable along track 46 and/or track pathway 48, as shown by arrows C in FIG. 4. In some embodiments, plate 60 is translated along track 46 to position plate 60 with vertebra V1. Plate 60 is translated between lateral axis limit 50 and oblique axis limit 52 to facilitate proper positioning of plate 60 relative to cage 12 and vertebra V1. Plate 60 is rotated into position such that portion 72 is oriented to engage vertebra V1, as shown in FIG. 5. Translation and rotation of plate 60 allows selective manipulation of plate 60 to facilitate plate 60 positioning relative to vertebra V1. In some embodiments, inserter I or other surgical instrument, as described herein, engages portion 72 and/or surface 66 to rotate plate 60, in a clockwise or counter-clockwise direction, about opening 68 such that opening 76 is selectively aligned with vertebral level V1 for orienting fastener 120 for fixation of cage 12 and/or plate 60 with vertebral level V1. In some embodiments, plate 60 can be rotated to align opening 76 with a superior vertebral body such as vertebral level V1 or an inferior vertebral body such as vertebral level V2 for orienting fastener 120 to fix cage 12 and/or plate 60 with tissue.

Fastener 120 is aligned with opening 76 and tissue, and inserted along inserter I via a driver 140. Fastener 120 is disposed with opening 76 such that fastener 120 engages vertebra V1. Driver 140 is configured to drive, torque, insert or otherwise fasten fastener 120 with vertebra V1 adjacent an intervertebral space S. In some embodiments, driver 140 may include surgical navigation components, as described herein, to establish a pathway for fastener 120 that is substantially concurrent with and/or parallel to the surgical approach angle. In some embodiments, plate 60 is fixed with fastener 120 at an oblique angle relative to cage 12. In some embodiments, plate 60 is fixed with fastener 120 laterally with cage 12.

Figure 6:
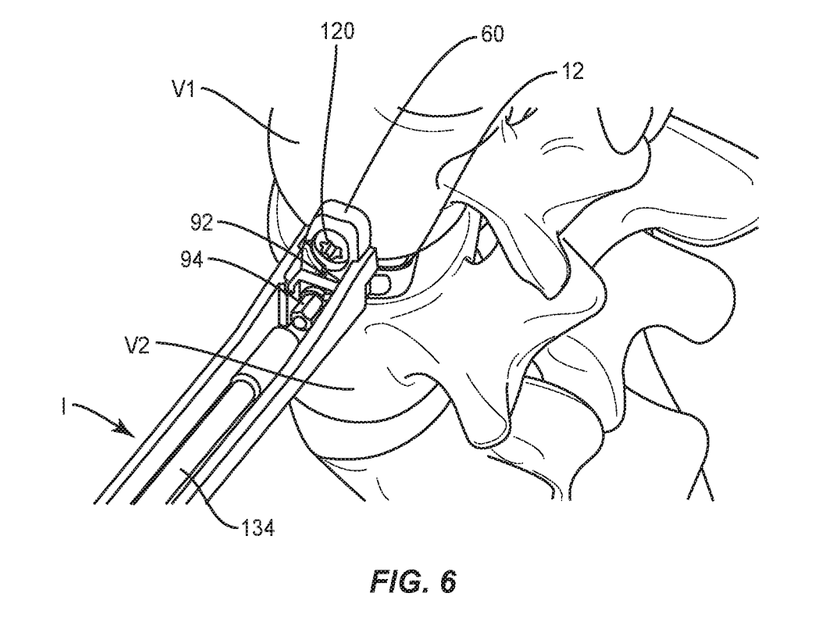
FIG. 6 is a perspective view of the components and vertebrae shown in FIG. 5.
Figure 7:
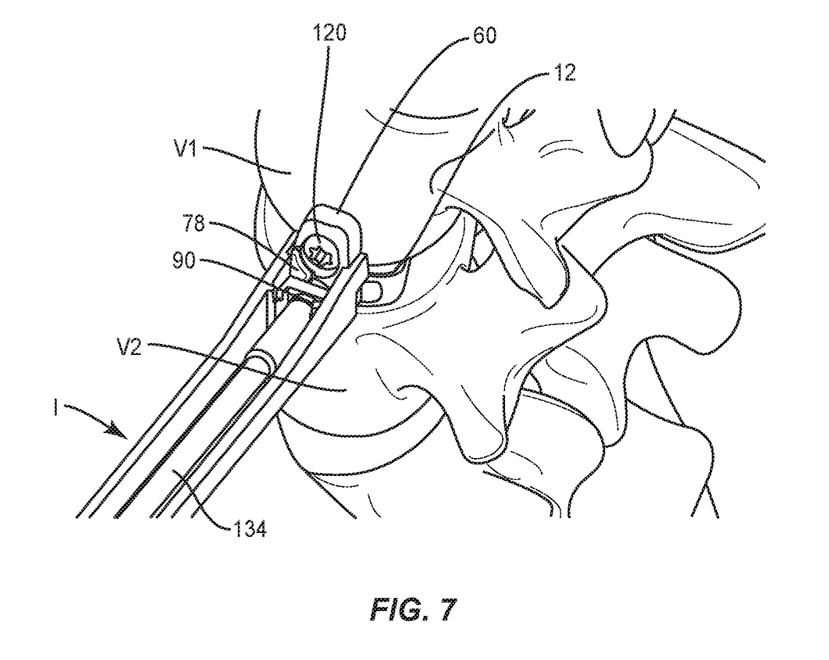
FIG. 7 is a perspective view of the components and vertebrae shown in FIG. 5.

Driver 134 is disposed with inserter I and rotated to fix plate 60 with cage 12, as shown in FIGS. 6-8. In some embodiments, plate 60 is configured for removable fixation with cage 12 such that plate 60 can be adjusted in situ and/or removed during a post-operative procedure. Driver 134 is rotated in a clockwise direction to manipulate set screw 90 such that portion 94 separates from portion 92 at a predetermined force and/or torque limit, as described herein. Portion 94 is removed from inserter I.

Tab 78 is initially disposed in a non-locking orientation, as shown in FIG. 9. In some embodiments, driver 140 is engaged with tab 78, as described herein, to actuate rotation of tab 78. Tab 78 is rotated into a locking orientation, as shown in FIG. 10. In the locking orientation, protrusion 102 extends over and/or overlaps a portion of fastener 120 to resist and/or prevent backout of fastener 120 from plate 60 and/or vertebra V1 through opening 76 and protrusion 104 extends over and/or overlaps a portion of set screw 90 to resist and/or prevent backout of set screw 90 from plate 60 and/or cage 12 through opening 68.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 11:
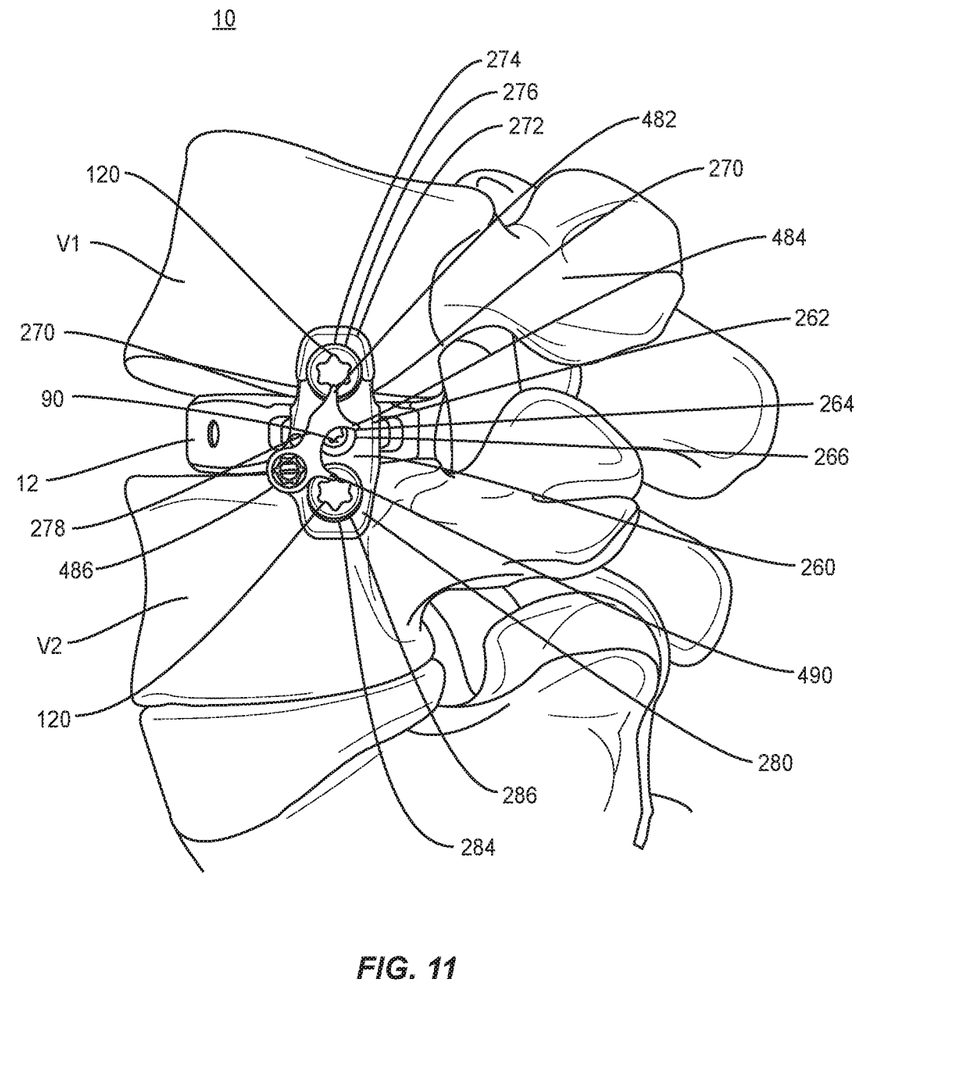
FIG. 11 is a perspective view of components of one embodiment of a surgical system in accordance with the principles of the present disclosure disposed with vertebrae.

In one embodiment, as shown in FIG. 11, spinal implant system 10, similar to the systems and methods described herein, includes cage 12, similar to that described herein and a plate 260, similar to plate 60 described herein. Plate 260 includes a surface 262 and a surface 264. Plate 260 includes a surface 266 that defines an opening 268. Opening 268 extends between surfaces 262, 264. Opening 268 is configured to receive set screw 90 for connecting cage 12 and plate 260, similar to that described herein. Opening 268 is configured for alignment with track 46 and facilitates engagement of set screw 90 with member 54, as described herein. Plate 260 includes instrument engagement surfaces 270. Surfaces 270 are configured to engage an instrument, such as, for example, an inserter I, as described herein.

Plate 260 includes a portion 272 configured to engage a vertebral level V1 and a portion 280 configured to engage a vertebral level V2. Portion 272 includes a surface 274 that defines an opening 276. Opening 276 extends between surfaces 262, 264. Opening 276 is configured to receive a fastener 120, as described herein, and to align fastener 120 for fixation with vertebral level V1. Portion 280 includes a surface 284 that defines an opening 286. Opening 286 extends between surfaces 262, 264. Opening 286 is configured to receive a fastener 120, as described herein, and to align fastener 120 for fixation with vertebral level V2.

In some embodiments, plate 260 includes a capture tab 278, similar to tab 78 described herein. Tab 278 is configured as a rotating cam lock having a protrusion 482, a protrusion 484 and a protrusion 490. Protrusion 482 extends over and/or overlaps all or a portion of fastener 120 to resist and/or prevent backout of fastener 120 from plate 260 and/or vertebra V1 through opening 276. Protrusion 484 extends over and/or overlaps all or a portion of set screw 90 to resist and/or prevent backout of set screw 90 from plate 260 and/or cage 12 through opening 268. Protrusion 490 extends over and/or overlaps all or a portion of fastener 120 to resist and/or prevent backout of fastener 120 from plate 260 and/or vertebra V2 through opening 286. Tab 278 includes a portion 486, similar to portion 106 described herein, configured to facilitate movement of protrusions 482, 484, 490 between a non-locking orientation and a locking orientation relative to fasteners 120 and set screw 90.

Figure 12:
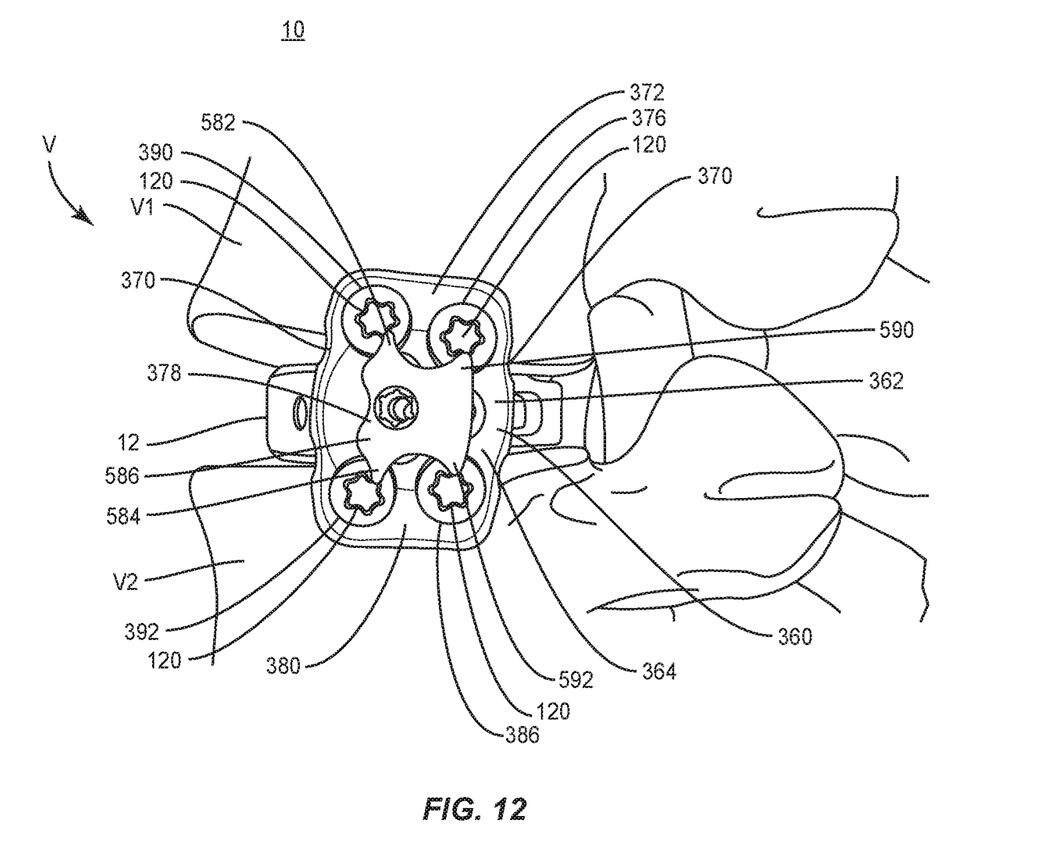
FIG. 12 is a perspective view of components of one embodiment of a surgical system in accordance with the principles of the present disclosure disposed with vertebrae.

In one embodiment, as shown in FIG. 12, spinal implant system 10, similar to the systems and methods described herein, includes cage 12, similar to that described herein and a plate 360, similar to the plates described herein. Plate 360 includes a surface 362 and a surface 364. In some embodiments, plate 360 includes a substantially rectangular configuration. In some embodiments, plate 360 can be variously configured, such as, for example, tubular, oval, oblong, triangular, square, polygonal, irregular, uniform, non-uniform, variable, hollow and/or tapered. In some embodiments, plate 360 may be attached with cage 12 prior to implantation or in situ. In some embodiments, plate 360 is removably connected with cage 12.

Plate 360 includes a surface that defines an opening (not shown), similar to opening 68, which extends between surfaces 362, 364 and is configured to receive set screw 90 for connecting cage 12 and plate 360, similar to that described herein. Plate 360 includes instrument engagement surfaces 370. Surfaces 370 are configured to engage an instrument, such as, for example, an inserter I, as described herein.

Plate 360 includes a portion 372 configured to engage a vertebral level V1 and a portion 380 configured to engage a vertebral level V2. Portion 372 includes an opening 376 and an opening 390. Openings 376, 390 extend between surfaces 362, 364. Openings 376, 390 are configured to receive fasteners 120, as described herein, and to align fasteners 120 for fixation with vertebral level V1. Portion 380 includes an opening 386 and an opening 392. Openings 386, 392 extend between surfaces 362, 364. Openings 386, 392 are configured to receive fasteners 120, as described herein, and to align fasteners 120 for fixation with vertebral level V2.

In some embodiments, plate 360 includes a capture tab 378, similar to the tabs described herein. Tab 378 is a rotating cam lock having a protrusion 582, a protrusion 584, a protrusion 590 and a protrusion 592. Protrusions 582, 590 extend over and/or overlap all or a portion of fasteners 120 to resist and/or prevent backout of fasteners 120 from plate 360 and/or vertebra V1 through openings 376, 390. Protrusions 584, 592 extend over and/or overlap all or a portion of fasteners 120 to resist and/or prevent backout of fasteners 120 from plate 360 and/or vertebra V2 through openings 386, 392. In some embodiments, tab 378 is configured to extend over and/or overlap all or a portion of set screw 90 to resist and/or prevent backout of set screw 90 from plate 260 and/or cage 12. Tab 378 includes a portion 586, similar to portion 106 described herein, configured to facilitate movement of protrusions 582, 584, 590, 592 between a non-locking orientation and a locking orientation relative to fasteners 120 and set screw 90.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a coupling member;
   an implant; and
   a plate defining a cavity having a cam lock positioned therein, the cam lock comprising a protrusion, the plate including a first opening and a second opening, the second opening being positioned between the cavity and the first opening, the cam lock being movable between a first orientation in which the protrusion overlaps the openings and a second orientation in which the protrusion is spaced apart from the openings, the implant comprising a body and a ball screw positioned in the body, the coupling member being connected to a post of the ball screw to provide topple of the plate relative to the implant.

2. A spinal implant as recited in claim 1, wherein the first opening is oriented to implant a fastener and the second opening is configured for disposal of the coupling member.

3. A spinal implant as recited in claim 1, wherein the coupling member has a first portion that is disposed in the second opening and a second portion having a threaded outer surface that engages a threaded inner surface of the post to connect the plate with the implant.

4. A spinal implant as recited in claim 3, wherein the portions are connected at a reduced diameter portion that is frangibly connected to the first portion.

5. A spinal implant as recited in claim 1, wherein the body includes a track, the ball being configured for engagement with and translation along the track.

6. A spinal implant as recited in claim 1, wherein the plate is selectively fixable with and adjustable relative to an outer surface of the implant.

7. A spinal implant as recited in claim 1, wherein the first opening has a diameter that is larger than a diameter of the second opening.

8. A spinal implant as recited in claim 1, wherein the second opening is closer to the cavity than the first opening.

9. A spinal implant as recited in claim 1, wherein the coupling member has a threaded outer surface that engages a threaded inner surface of the post.

10. A spinal implant comprising:
    a coupling member;
    an implant; and
    a plate defining a cavity having a cam lock positioned therein, the cam lock comprising a protrusion, the plate including a first opening, a second opening and a third opening, the second opening being positioned between the first opening and the third opening, the cavity being positioned between the first opening and the second opening, the cam lock being movable between a first orientation in which the protrusion overlaps the openings and a second orientation in which the protrusion is spaced apart from the openings, the implant comprising a body and a ball screw positioned in the body, the coupling member being connected to a post of the ball screw to provide toggle of the plate relative to the implant.

11. A spinal implant as recited in claim 10, wherein the first and third openings are each oriented to implant a fastener and the second opening is configured for disposal of the coupling member.

12. A spinal implant as recited in claim 10, wherein the coupling member has a first portion that is disposed in the second opening and a second portion having a threaded outer surface that engages a threaded inner surface of the post to connect the plate with the implant.

13. A spinal implant as recited in claim 10, wherein the body includes a track, the ball being configured for engagement with and translation along the track.

14. A spinal implant as recited in claim 10, wherein the plate is selectively fixable with and adjustable relative to an outer surface of the implant.

15. A spinal implant as recited in claim 10, wherein the first opening and the third opening each have a diameter that is larger than a diameter of the second opening.

16. A spinal implant as recited in claim 10, wherein the cavity is closer to the first opening than the third opening.

17. A spinal implant as recited in claim 10, wherein the coupling member has a threaded outer surface that engages a threaded inner surface of the post.

18. A spinal implant comprising:
    a coupling member;

an implant; and a plate defining a cavity having a cam lock positioned therein, the cam lock comprising a protrusion, the plate including a first opening, a second opening, a third opening, a fourth opening and a fifth opening, the cavity being positioned between the first opening and the third opening, the fifth opening being positioned between the second opening and the fourth opening, the cam lock being movable between a first orientation in which the protrusion overlaps the openings and a second orientation in which the protrusion is spaced apart from the openings, the implant comprising a body and a ball screw positioned in the body, the coupling member being connected to a post of the ball screw to provide toggle of the plate relative to the implant, the body including a track, the ball being configured for engagement with and translation along the track.

19. A spinal implant as recited in claim 18, wherein the first, second, third and fourth openings are each oriented to implant a fastener and the fifth opening is configured for disposal of the coupling member.

20. A spinal implant as recited in claim 18, wherein the first, second, third and fourth openings each have a diameter that is greater than a diameter of the fifth opening.

21. A spinal implant as recited in claim 18, wherein the coupling member has a threaded outer surface that engages a threaded inner surface of the post.

\* \* \* \* \*